US007043974B2

(12) United States Patent
Grossman et al.

(10) Patent No.: US 7,043,974 B2
(45) Date of Patent: May 16, 2006

(54) MULTIPLE-BLOWER RELATIVE HUMIDITY CONTROLLED TEST CHAMBER

(75) Inventors: Douglas M. Grossman, Fairview Park, OH (US); Gregory R. Fedor, Bay Village, OH (US); William R. Wurst, Elyria, OH (US); Danny J. Fayak, Wellington, OH (US)

(73) Assignee: Q-Panel Lab Products Corporation, Westlake, OH (US)

( * ) Notice: Subject to any disclaimer, the term of this patent is extended or adjusted under 35 U.S.C. 154(b) by 0 days.

(21) Appl. No.: 11/101,831

(22) Filed: Apr. 8, 2005

(65) Prior Publication Data

US 2005/0178219 A1 Aug. 18, 2005

Related U.S. Application Data

(63) Continuation of application No. 10/343,483, filed as application No. PCT/US01/28885 on Sep. 17, 2001, now Pat. No. 6,892,591.

(60) Provisional application No. 60/233,083, filed on Sep. 15, 2000.

(51) Int. Cl.
*G01L 5/04* (2006.01)

(52) U.S. Cl. ........................................ 73/159; 73/865.6

(58) Field of Classification Search ................ 165/213, 165/214

See application file for complete search history.

(56) References Cited

U.S. PATENT DOCUMENTS

| | | | | |
|---|---|---|---|---|
| 3,488,681 | A | 1/1970 | Mita | |
| 3,886,791 | A | 6/1975 | Grossman et al. | |
| 4,704,903 | A | 11/1987 | Suga et al. | |
| 4,760,748 | A | 8/1988 | Katayanagi et al. | |
| 4,843,893 | A | 7/1989 | Huber et al. | |
| 4,964,298 | A * | 10/1990 | Matsushita | 73/117.1 |
| 5,005,636 | A * | 4/1991 | Haessig | 165/214 |
| 5,395,494 | A * | 3/1995 | Anderson et al. | 205/785.5 |
| 6,502,470 | B1 * | 1/2003 | Taylor et al. | 73/864.35 |

* cited by examiner

*Primary Examiner*—Robert Raevis

(74) *Attorney, Agent, or Firm*—Fay, Sharpe, Fagan, Minnich & McKee, LLP

(57) ABSTRACT

An accelerated weathering apparatus includes a test chamber (30), a specimen supporting means (34), a light source (60) powered by a power source controlled by a ballast, at least one chamber air temperature sensor (26), a black panel temperature sensor (36), and a multiple blower system and control means (52). A first blower (12) draws and circulates outside or fresh air and as second blower (46) optionally draws recirculated air into an air mixing duct. The speeds of the fresh air and recirculated air are independently regulated and controlled by a blower controller based on the chamber air temperature and black panel temperature, respectively. In addition, a humidifier (18) and humidity controller (20) regulates humidity within the system as required.

9 Claims, 5 Drawing Sheets

10
Humidity Controller
20
18
22
24
26
60
30
36
32
34
40
42
44
16
48
14
50
46
12
Blower Controller
52

Recirculation Air Blower
46
Fresh Air Blower
12
Motor Controller
76
Motor Controller
78
Second Cat Sensor
42
Comparison Processor
74
BPT Sensor
36
First Cat Sensor
26
Set Point Means
70
52

MULTIPLE-BLOWER RELATIVE HUMIDITY CONTROLLED TEST CHAMBER

This application is a continuation of U.S. application Ser. No. 10/343,483 now U.S. Pat. No. 6,892,591, filed Jan. 30, 2003, which is a national filing of PCT/US01/28885, filed Sep. 17, 2001, which claims the benefit of U.S. Provisional Application Ser. No. 60/233,083, filed Sep. 15. 2000.

BACKGROUND OF THE INVENTION

The present invention relates to the art of testing specimens for resistance to deterioration due to sunlight and humidity. It finds particular application in conjunction with a materials test chamber having a controlled multiple-blower system to achieve simultaneous air and black panel temperature control and/or relative humidity control. However, it will be appreciated that the invention has broader applications and may be advantageously employed in connection with other accelerated weather testing devices and concepts.

In accelerated weather testing, a specimen is supported within a test chamber and exposed to ultraviolet fluorescent lamps, such as xenon lamps. Typically, outside air or fresh air is heated and blown into the interior of the test chamber in order to regulate the temperature within the chamber. In addition, humidity is added to the chamber in the form of evaporated water. In the above-described weathering apparatus, one example of the machine's operation includes applying ultraviolet light rays to one or more specimens of a set temperature for a given period of time. The lamps are then turned off and the interior of the chamber is kept at the same or a different temperature for a set period of time. Further, humidity may be added to the system in a repeated fashion. Accordingly, specimens are wetted, exposed to ultraviolet rays, and dried in a repeated fashion.

In the weathering system described above, the chamber air temperature (CAT) is regulated using a single blower system, that is a single blower which draws outside or fresh air into the system, along with a damper to regulate air flow. While the single blower system is fairly adequate for controlling chamber air temperature, it is inadequate for precise humidity control as well as simultaneous control of the CAT and black panel temperature (BPT). Typically, black panel temperature is measured using a temperature sensor placed on the specimen support to measure the actual black panel temperature, that is, the temperature of a dark specimen disposed within the test chamber. Because a single blower and damper system is not fully equipped to effectively regulate both chamber air temperature and black panel temperature along with precise humidity control, a need exists for a system and control method for simultaneous control of both CAT and BPT.

The present invention is directed to a multiple blower system and control method for the simultaneous regulation of chamber air temperature and black panel temperature, which overcomes the above-referenced problems and others.

SUMMARY OF THE INVENTION

In accordance with one aspect of the present invention, an accelerated weathering apparatus includes a test chamber, a specimen support, and a light source powered by a power source controlled by a ballast. A pair of chamber air temperature sensors disposed before and after the test chamber measure chamber air temperature. A black panel temperature sensor measures the black panel temperature within the test chamber. An air heater heats air passing through the system. A dual blower system draws and circulates fresh and recirculated air through the system. The dual blower system includes a fresh air blower and a recirculation air blower. In this apparatus, a method for controlling both air and black panel temperature within the test chamber includes selecting a desired irradiance and selecting both a desired chamber air temperature and a desired black panel temperature. The chamber air temperature and the black panel temperature are sensed. The sensed chamber air temperature is compared to the selected chamber air temperature, while the sensed black panel temperature is compared to the selected black panel temperature. In response to the comparing steps, the speed of at least one of the fresh air blower and the recirculation air blower is adjusted.

In accordance with a more limited aspect of the present invention, if the sensed black panel temperature is greater than the selected black panel temperature, the speed of the fresh air blower is increased.

In accordance with a more limited aspect of the present invention, if the sensed chamber air temperature is greater than the selected chamber air temperature, the speed of the recirculation air blower is decreased.

In accordance with a more limited aspect of the present invention, the method further includes selecting a desired relative humidity and sensing the relative humidity. The sensed and selected relative humidities are compared and, in response to this comparison, the speed of at least one of the fresh air blower and the recirculation air blower is adjusted.

In accordance with a more limited aspect of the present invention, if the sensed black panel temperature is less than the selected black panel temperature, the total blower speed is decreased.

In accordance with a more limited aspect of the present invention, if the sensed chamber air temperature is less than the selected chamber air temperature, the fraction of fresh air drawn into the system is decreased, where the fraction of fresh air is a ratio of the fresh air blower speed to the total blower speed.

In accordance with a more limited aspect of the present invention, if the sensed chamber air temperature is less than the selected chamber air temperature, a blower speed ratio is decreased, where the blower speed ratio is a ratio of the fresh air blower speed to the recirculation air blower speed.

In accordance with another aspect of the present invention, an accelerated weather testing apparatus includes a test chamber, a specimen supporting means, irradiance sources, a chamber air temperature sensor, and a black panel temperature sensor. A fresh air blower and a recirculation air blower are controlled by control means, while humidity is controlled by a humidifier and humidity control means. In this apparatus, a method of accelerated weather testing includes selecting a desired irradiance, chamber air temperature (CAT), black panel temperature (BPT), and relative humidity. A specimen is irradiated in accordance with a selected irradiance. Fresh air is drawn into the testing apparatus with the fresh air blower at an initial fresh air blower speed. Humidity is added to the fresh air. The humidified fresh air is heated and circulated through the test chamber. The CAT is sensed as air exits the test chamber and the BPT is sensed. A portion of the air exiting the test chamber is recirculated using the recirculation air blower at an initial recirculation air blower speed such that the recirculated air mixes with fresh air drawn in by the fresh air blower.

In accordance with a more limited aspect of the present invention, the method further includes comparing the selected CAT to the sensed CAT. The selected BPT is compared to the sensed BPT. In response to the comparing steps, at least one of the $S_F$ and $S_R$ are adjusted.

In accordance with another aspect of the present invention, an accelerated weathering apparatus includes a test chamber and a specimen supporting means for supporting specimens within the test chamber. A light source, which is disposed within the test chamber, produces light in the test chamber. A power source powers the light source and is controlled by ballast means. Air is circulated through a duct system within the weathering apparatus, where the duct system includes an air mixing duct, in which fresh air and recirculated air mix, a chamber inlet duct disposed between the air mixing duct and a first end of a test chamber, and an exhaust duct disposed between a second end of the test chamber and an exhaust. At least one test chamber air temperature sensor is disposed in at least one of the chamber inlet duct and the exhaust duct. A black panel temperature sensor is disposed adjacent the specimen supporting means for measuring one of black panel temperature and black standard temperature. A multiple blower system circulates air through the test chamber. The multiple blower system includes a fresh air blower, which draws room air into the air mixing duct through a fresh air inlet, and a recirculation air blower which optionally draws air from the exhaust duct into the air mixing duct through a recirculation inlet. A blower controller controls the speed of the fresh air blower and the recirculation air blower.

In accordance with a more limited aspect of the present invention, the blower controller includes a set-point means for generating and sending a plurality of set point signals. A comparison processor compares the set point signals to a sensed temperature signal from at least one of the black panel temperature sensor and the test chamber air temperature sensor. A pair of motor controllers control the fresh air and the recirculation air blowers in accordance with signals received from the comparison processor.

DETAILED DESCRIPTION OF THE PREFERRED EMBODIMENTS

Figure 1:
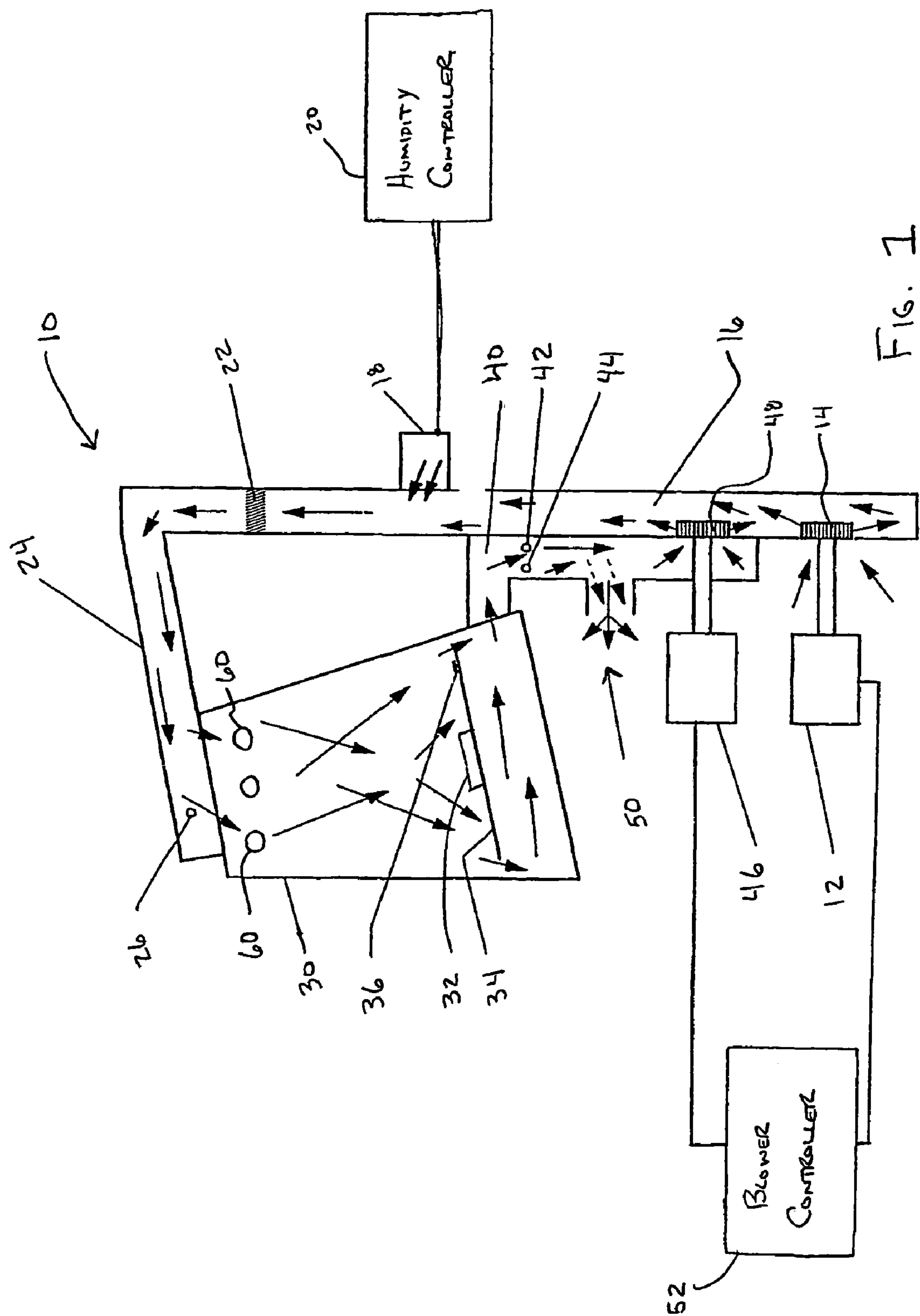
FIG. 1 is a diagrammatic illustration of an accelerated weathering apparatus including a controlled multiple blower system in accordance with the present invention.

With reference to FIG. 1, an accelerated weathering apparatus 10 includes a fresh air blower 12, which draws room air or fresh air through a fresh air inlet 14 into an air mixing duct 16. The fresh air travels through the air mixing duct 16 where a humidifier 18, controlled by a humidity controller 20, adds additional humidity to the air as needed. Optionally, air heater 22 increases the temperature of the air, if needed, before the air flows into a chamber inlet duct 24. It is to be understood that the plurality of arrows present in FIG. 1 are to illustrate the pattern of air flow throughout the accelerated weathering apparatus.

Optionally, the air temperature may be measured by a first air temperature sensor 26, the operation of which will be described more fully below, before passing into a test chamber 30. The air flows into the test chamber and over one or more samples 32 disposed on a specimen supporting means 34, such as a sample tray. Preferably, a black panel temperature 36 sensor is mounted to the specimen supporting means 34.

After passing around the sample tray, the air flows out of the test chamber 30 and into an exhaust duct 40, where a second chamber air temperature sensor 42 and a chamber humidity sensor 44 measure the exhaust air temperature and either relative humidity or wet bulb temperature. At this point, a recirculation air blower 46 optionally draws a portion of the air from the exhaust duct back into an air mixing duct 16 through a recirculated air inlet 48, where it mixes with the fresh air drawn in by the fresh air blower 12, for circulation through the system again. Air that is not drawn back into the system through the recirculation air blower 46 flows out of the system through an exhaust 50. As is described more fully below, a blower controller 52 controls the speeds of the fresh air blower 12 and a recirculation air blower 46 in order to control both the chamber air and black panel temperatures. While FIG. 1 illustrates an embodiment containing two air blowers, it is to be appreciated that the present invention is applicable to other multiple-blower systems.

Prior to performing a test in the weathering apparatus 10, an operator specifies or sets the applicable test parameters. Preferably, the desired irradiance ($IRR_{SP}$) and at least one of the following: (i) the desired black panel temperature ($BPT_{SP}$), and (ii) desired chamber air temperature ($CAT_{SP}$) are set. In addition, the desired relative humidity ($RH_{SP}$) may be selected by the operator if the test to be performed requires such. It is to be appreciated that if only one of the CAT and BPT is specified, the other is estimated, either by formula or through a lookup table.

Artisans will appreciate that actual chamber air temperature (CAT) cannot be measured directly in the test chamber 30, because of the heating effect of the radiation from the lamps 60. Therefore, chamber air temperature is typically measured at the chamber outlet using the second chamber air temperature sensor 42. Alternately, the actual chamber air temperature or dry bulb temperature is measured using an average of the temperature readings from the first chamber air sensor 26, which is located at the test chamber inlet, and the temperature reading of the second chamber air temperature sensor located at the chamber outlet. It is to be appreciated that either a weighted or simple average of the temperatures from the first and second chamber air temperature sensors may be employed.

In one embodiment, the black panel temperature sensor 36 includes an uninsulated black panel sensor, which measures actual black panel temperature (BPT). Alternately, the black panel temperature sensor 36 includes an insulated black panel sensor which measures actual black standard temperature (BST). It is to be appreciated that in the below-described control methods, BPT and BST may be used interchangeably, depending on the requirements of the weathering test being performed. In one embodiment, the chamber humidity sensor 44 includes a conventional relative humidity sensor. In an alternate embodiment, relative humidity is calculated or looked up based on measurements from a wet-bulb temperature sensor, along with temperature readings from one or both of the chamber air temperature sensors 26, 42, which provide dry bulb temperatures.

Figure 2:
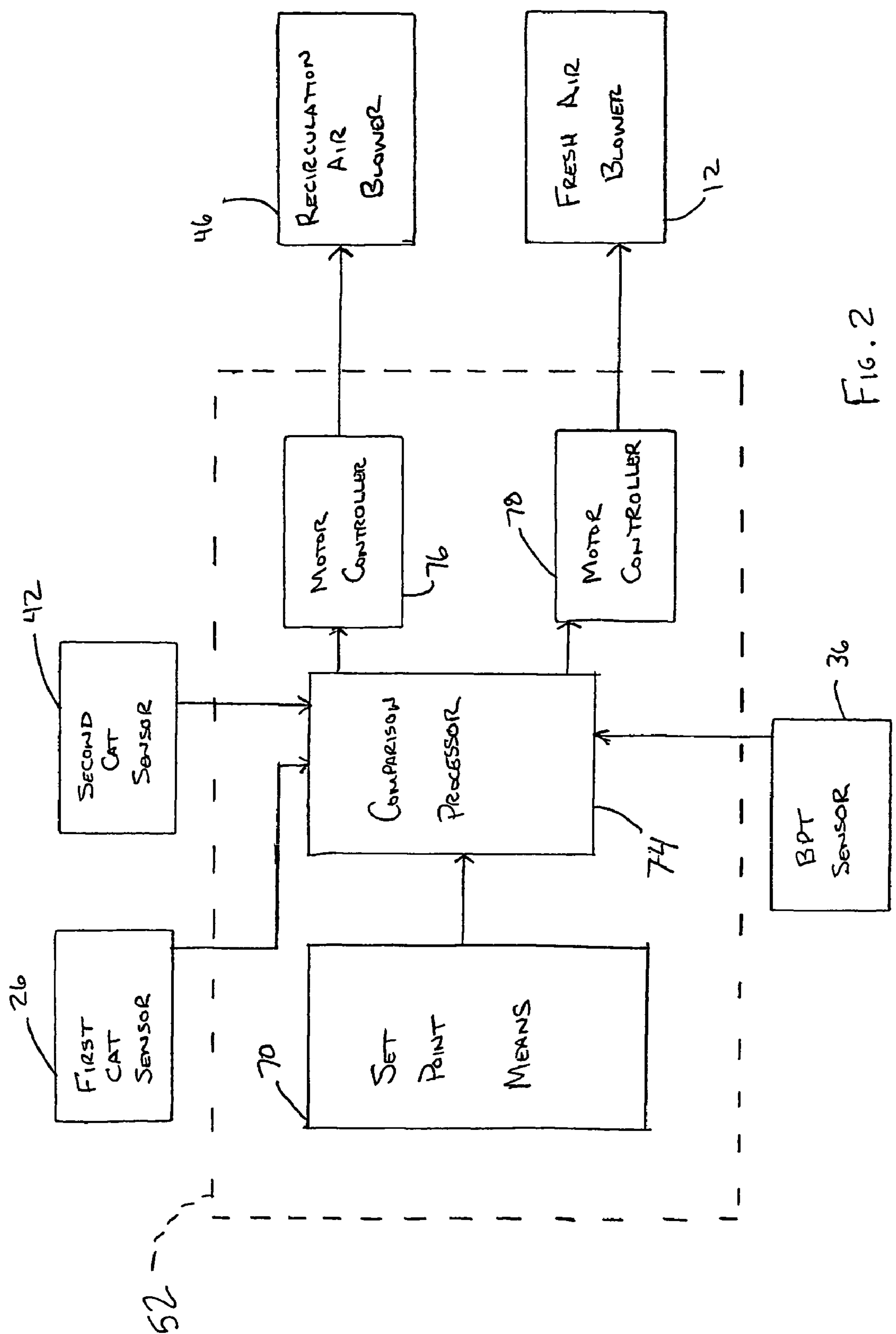
FIG. 2 is a diagrammatic illustration of the blower controller in accordance with the present invention.

With reference to FIG. 2 and continuing reference to FIG. 1, where like reference numerals refer to like elements, the blower controller 52 includes a set point means 70, which receives and stores the desired temperature parameters such as $BPT_{SP}$ and $CAT_{SP}$. A comparison processor 74 receives the desired test parameters from the set point means 70 along with CAT readings and BPT readings from the first and second CAT sensors 26, 42 and the BPT sensor 36. As is described more fully below, the comparison processor 74 compares the desire test parameters with the measured parameters and sends motor controller signals to a pair of motor controllers 76, 78, which in turn control the fan speeds of the fresh air blower 12 and the recirculation air blower 46.

Figure 3:
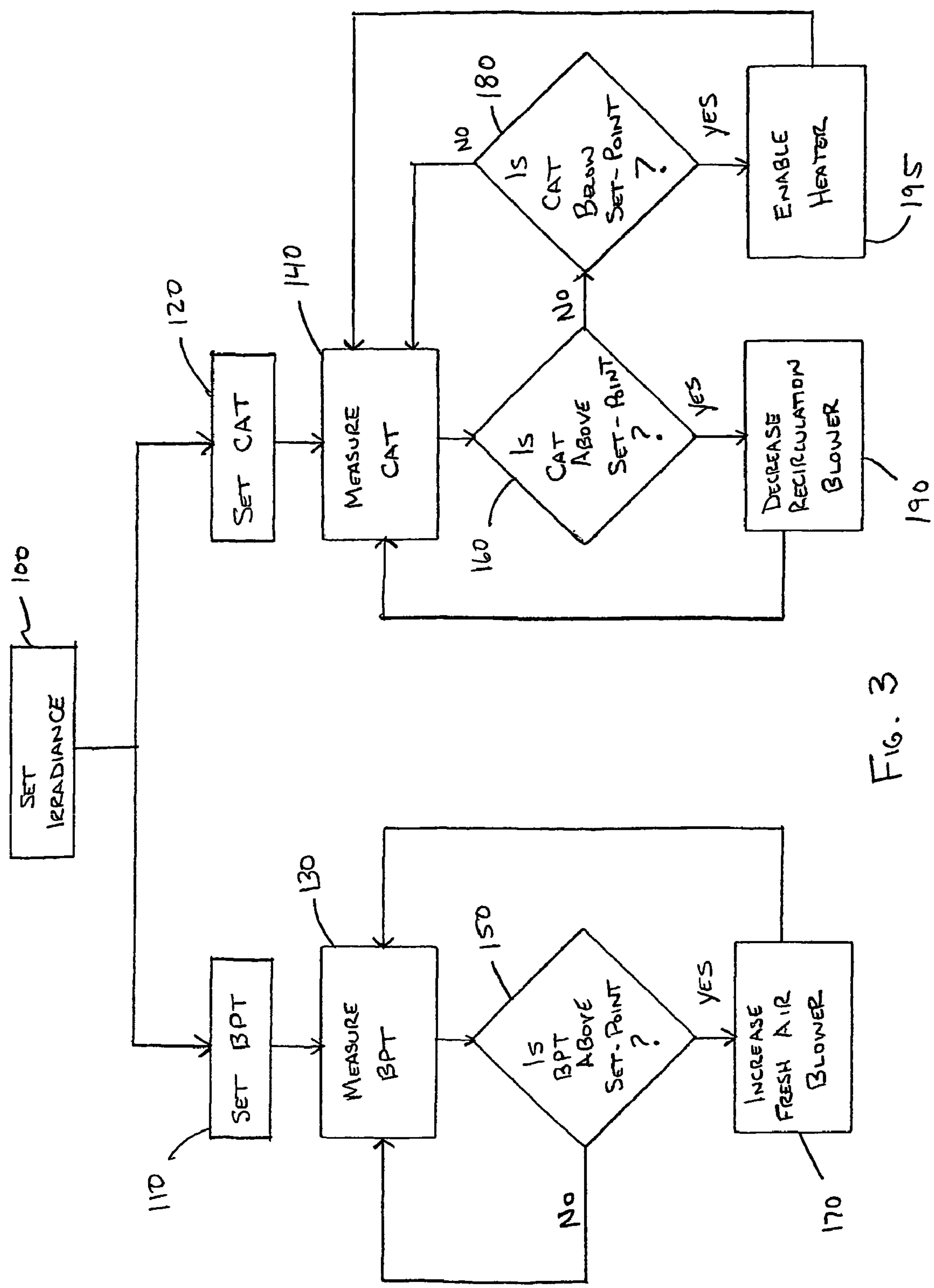
FIG. 3 is a flow chart illustrating a method of controlling a multiple blower system in accordance with the present invention.

With reference to FIG. 3, once the weathering apparatus is activated, the irradiance is set 100 and controlled to $IR_{SP}$ by the lamp ballasts in a conventional manner. The two-blower embodiment illustrated in FIGS. 1 and 2 is controlled by the blower controller 52. Both the black panel temperature (BPT) and chamber air temperature (CAT) are set 110, 120 for the given test. As air circulates throughout the system, the BPT is measured 130 and compared 150 to the set point to determine whether or not the BPT is above the set point $BPT_{SP}$. If the BPT is above the set point, the speed of the fresh air blower is increased 170 in order to compensate for the rise in temperature. That is, more fresh air is drawn into the air mixing duct through the fresh air inlet by the fresh air blower.

Concurrently, the chamber air temperature (CAT) is measured 140 and compared 160, 180 to the CAT set point, $CAT_{SP}$. More particularly, if the CAT is above the set point, the speed of the recirculation blower is decreased 190. Further, if the CAT is below the set point 180, the air heater is enabled 195. It is to be appreciated that in this embodiment the two blowers are controlled by the blower controller as two automatic closed-loop systems. That is, the speed of the fresh air blower ($S_F$) controls and is determined by the BPT, while the speed of the recirculation air blower ($S_R$) controls and is determined by the CAT. Alternately, the blower controller controls the two blowers as two automatic closed-loop systems where $S_F$ controls and is determined by CAT, while $S_R$ controls and is determined by BPT. In this embodiment, as the measured temperatures rise, the respective blowers increase in speed. In this embodiment, the air heater may be used in conjunction with the fresh air blower to provide an additional range for the CAT.

Figure 4:
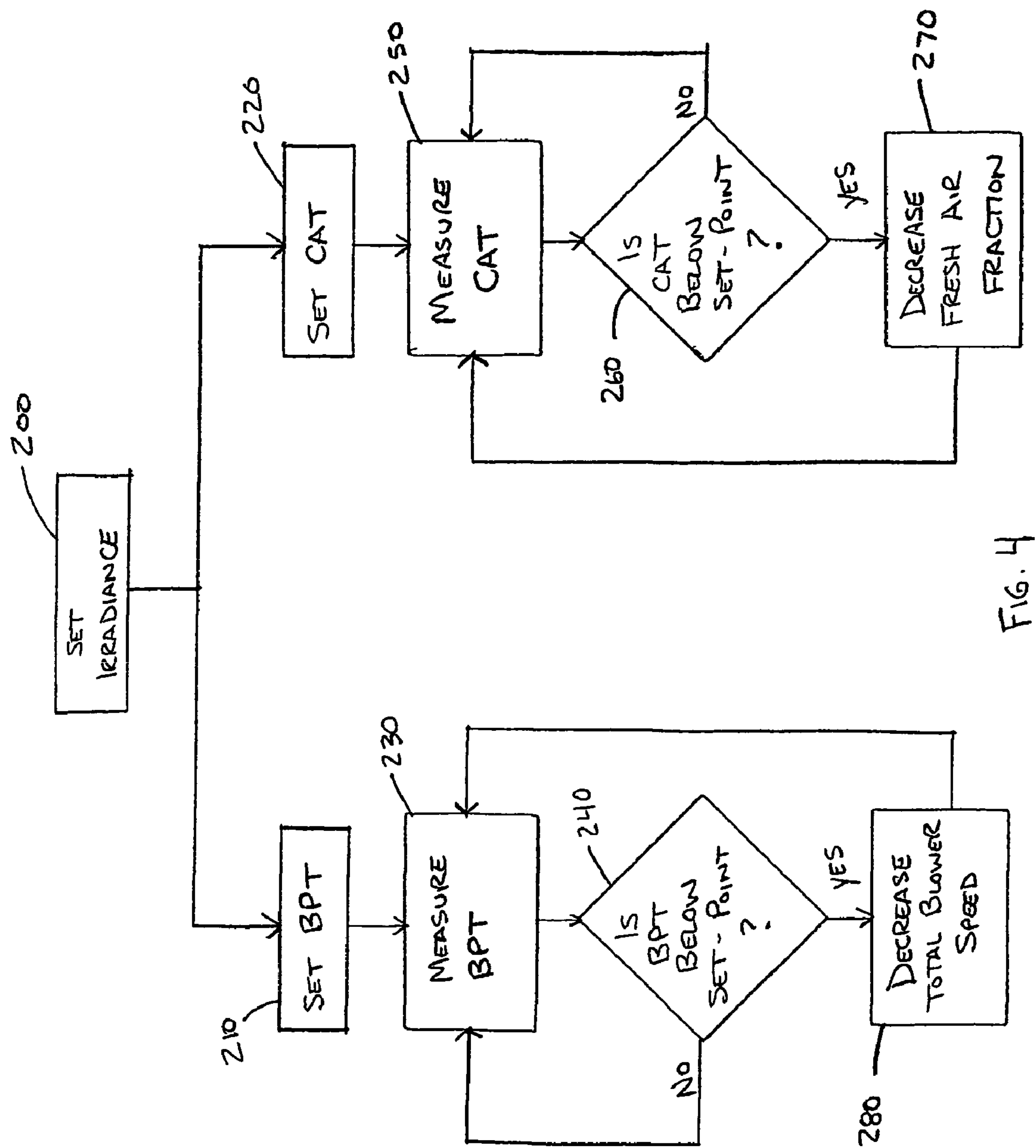
FIG. 4 is a flow chart illustrating another preferred method of controlling a multiple blower system in accordance with the present invention.

With reference to FIG. 4, in an alternate embodiment, the blower controller controls the two blowers as one automatic closed-loop system, with two outputs to control the two blower speeds. In this embodiment, the total blower speed ($S_{TOTAL}=S_F+S_R$) controls and is determined by the black panel temperature (BPT), while the fraction of fresh air ($R_{FRESH}=S_F/S_{TOTAL}$), or a similar weighted ratio controls and is determined by the chamber air temperature CAT.

Initially, the desired irradiance is set 200. In addition, the desired BPT and CAT are set 210, 220. The measured BPT is compared 240 to the set BPT. In addition, the CAT is measured 250 and compared 260 to the CAT set point. In this embodiment, if the BPT is at the set point, and the CAT is below the set point, the fresh air fraction $R_{FRESH}$ is decreased 270, while the total blower speed $S_{TOTAL}$ is held constant. In other words, the speed of the fresh air blower is reduced while the speed of the recirculated air blower is increased. If the BPT is below the set point, while the CAT is at or above the set point, the fresh air fraction remains constant while the total blower speed is reduced. In other words, both the fresh air blower speed and the recirculated air blower speed are decreased. In this embodiment, the air heater may be used to increase the range of temperatures that is achievable.

Figure 5:
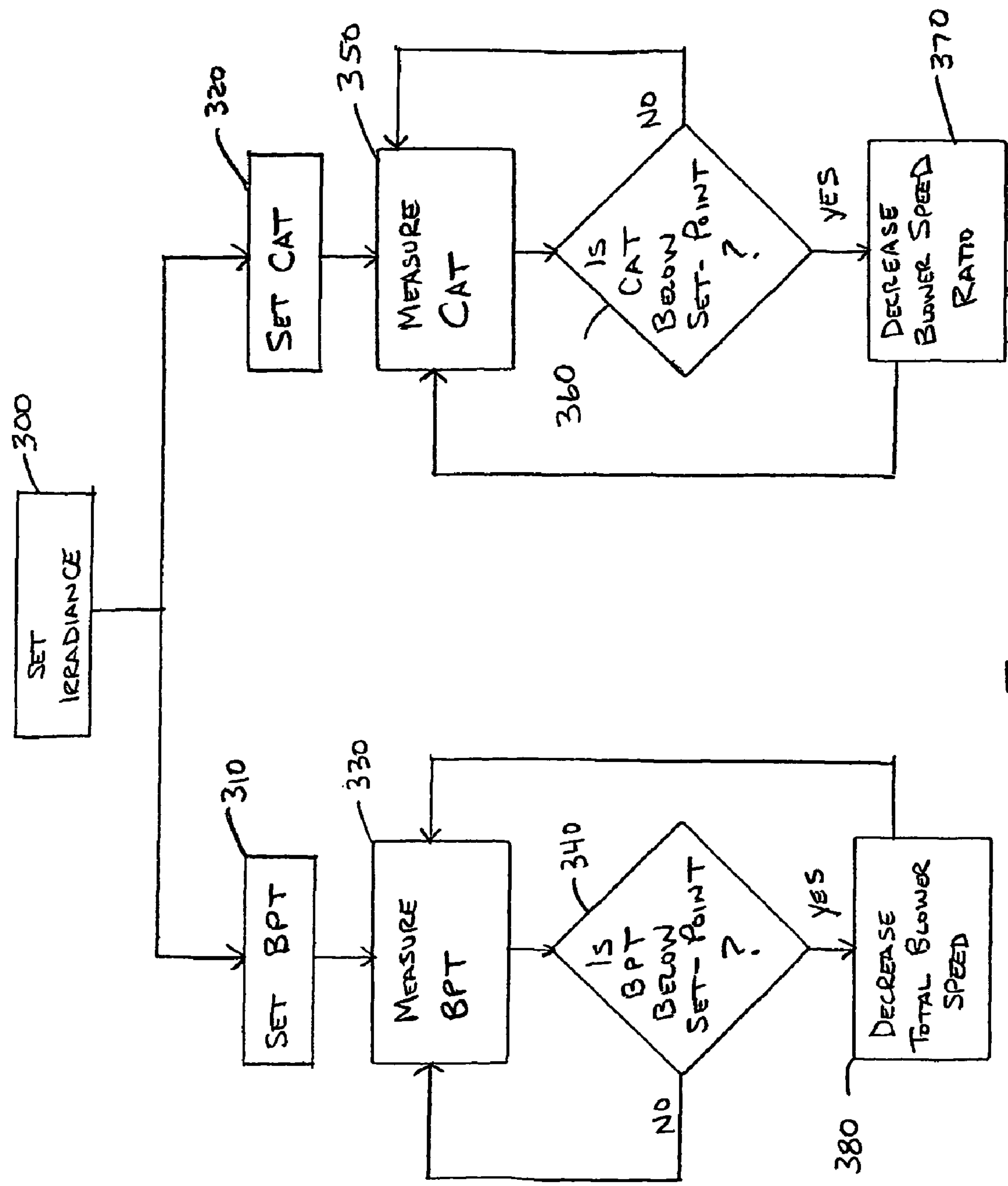
FIG. 5 is a flow chart illustrating another preferred embodiment for controlling a multiple blower system in accordance with the present invention.

With reference to FIG. 5, in an alternate embodiment, the total blower speed $S_{TOTAL}$ controls and is determined by the BPT, while a blower speed ratio ($R_{SPEED}=S_F/S_R$), or a similar weighted ratio (controls and is determined by the CAT.)

The radiance is set 300 to the desired value. In addition, the BPT and CAT are both set 310, 320 to their respective desired values. Both the BPT and CAT are measured 330, 350 and compared 340, 360 to the respective set points. In this embodiment, if the BPT is at the set point, but the CAT is below the set point, $S_{TOTAL}$ is held constant, while the blower speed ratio $R_{SPEED}$ is decreased 370. In other words, the fresh air blower speed $S_F$ is reduced, while the recirculated air blower speed $S_R$ is increased. Alternately, if the BPT is below the set point, while the CAT is at or above the set point, the blower speed ratio $R_{SPEED}$ remains constant while the total blower speed $S_{TOTAL}$ is decreased, that is, both $S_F$ and $S_R$ are decreased. In this embodiment, the air heater may be used to increase the range of achievable temperatures.

In an alternate embodiment, the blower controller controls the fresh air blower and the recirculation air blower as two open-loop systems. In this embodiment, the speed of the fresh air blower and the speed of the recirculation air blower are each independently controlled manually, such as with a potentiometer attached to a motor speed controller. By adjusting the two blower speeds, the BPT and CAT of the system are each adjusted, although somewhat interdependently, to fall within specified ranges. If desired, one or more air heaters are employed in conjunction with the fresh air and/or recirculated air blowers to provide a greater range of chamber temperatures.

It is to be appreciated that in any of the above-identified multiple-blower temperature control methods, the blower speeds may be held within fixed maximum and minimum values, and/or within floating maximum and minimum values, depending on the operation of each of the blowers. The floating limits are useful because a minimum speed of one blower is necessary to block the flow from the other blower passing the wrong way through it. For example, if 100% fresh air is required for a certain test, the fresh air blower spins at the speed which provides the needed airflow. However, if the recirculation air blower is stopped, a significant amount of fresh air reverse flows through the recirculated air blower and out the machine exhaust. To prevent this, the recirculation air blower is operated at a slower "blocking" speed, thereby stopping this leakage and providing the full output of the fresh air blower to the test chamber.

Further, if desired, once the blower speeds are established, the speed of the fresh air blower may be increased by a nominal amount, 10% for example, and the recirculation air blower adjusted to yield the equivalent total flow. In this embodiment, the air heater fine tunes the air temperature, yielding more stable temperatures.

Referring again to FIG. 1, the relative humidity within the test chamber 30 is controlled using a humidity controller 20, which operates manually, semi-automatically, or automatically.

The relative humidity inside the test chamber 30 is controlled using a humidity controller 20, which operates manually, semi-automatically, or automatically. The semi-automatic control embodiments require sensing the relative humidity directly, or calculating it using a sensed wet bulb temperature. A feedback mechanism within the humidity controller 20 directs the humidifier 18 to release more humidity as the measured relative humidity falls below the specified relative humidity $RH_{SP}$ or less as the RH exceeds $RH_{SP}$. The humidifier 18 takes form in at least one of a direct water spray, an air-atomized water spray, a mechanically generated water mist, an ultrasonic fog generation, that is, a nebulizer, or a water boiler. Further, the humidity controller may affect the operation of the two air blowers because relative humidity is "relative" to the air temperature. Therefore, control of the air temperature is important for controlling the relative humidity even if the specified test does not explicitly require temperature control. For example, if the RH is below the set point, the recirculation air blower will recirculate a higher percentage of air in order to retain and increase the relative humidity. In contrast, if the relative humidity is above the RH set point, the fresh air blower draws additional "dry" room air into the mixing air duct, while the recirculation blower recirculates less, and therefor exhausts more, "wet" air from the test chamber.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiment, the invention is now claimed to be:

1. A test apparatus comprising:

a test chamber having a fluid inlet and a fluid outlet;

a first blower in fluid communication with ambient and the fluid inlet;

a second blower in fluid communication with the fluid inlet and the fluid outlet;

a radiant energy source disposed in the test chamber;

a specimen support disposed in the test chamber;

a first temperature sensor for detecting chamber air temperature; and a controller in communication with the first temperature sensor and at least one of the first and second blowers.

2. The test apparatus of claim 1, further comprising a second temperature sensor disposed in the test chamber that is in communication with the controller.

3. The test apparatus of claim 2, wherein the first and second temperature sensors each comprise a sensor from a group comprising a black panel temperature sensor, a black standard temperature sensor, and a chamber air temperature sensor.

4. The test apparatus of claim 2, wherein the second temperature sensor comprises a black panel temperature sensor.

5. The test apparatus of claim 1, further comprising a humidifier in fluid communication with the test chamber.

6. The test apparatus of claim 5, further comprising a humidity sensor disposed adjacent the fluid outlet.

7. The test apparatus of claim 1, further comprising an air heater in fluid communication with the test chamber.

8. The test apparatus of claim 1, wherein the second blower is downstream from the fluid outlet.

9. The test apparatus of claim 8, wherein the second blower is positioned to recirculate air from the test chamber into an air mixing duct disposed upstream from the fluid inlet.

* * * * *